United States Patent
Kandori et al.

(10) Patent No.: US 8,118,758 B2
(45) Date of Patent: Feb. 21, 2012

(54) LIVING BODY INSPECTION APPARATUS

(75) Inventors: Akihiko Kandori, Tokyo (JP); Tsuyoshi Miyashita, Fuchu (JP); Mitsuru Onuma, Tokyo (JP); Yuko Sano, Kokubunji (JP); Ryuzo Kawabata, Kodaira (JP)

(73) Assignee: Hitachi Computer Peripherals Co., Ltd., Kanagawa-Ken (JP)

( * ) Notice: Subject to any disclaimer, the term of this patent is extended or adjusted under 35 U.S.C. 154(b) by 401 days.

(21) Appl. No.: 12/388,780

(22) Filed: Feb. 19, 2009

(65) Prior Publication Data

US 2009/0227907 A1    Sep. 10, 2009

(30) Foreign Application Priority Data

Mar. 10, 2008 (JP) ................................. 2008-058917

(51) Int. Cl.
*A61B 5/103* (2006.01)

(52) U.S. Cl. ........................................ 600/595; 600/593

(58) Field of Classification Search .................. 600/587, 600/593, 595, 586
See application file for complete search history.

(56) References Cited

U.S. PATENT DOCUMENTS

| 2005/0283096 A1* | 12/2005 | Chau et al. ..................... 600/593 |
| 2008/0147142 A1* | 6/2008 | Testerman et al. .............. 607/48 |
| 2008/0269646 A1* | 10/2008 | Chau et al. ..................... 600/595 |
| 2008/0306373 A1* | 12/2008 | Kandori et al. ................. 600/407 |
| 2009/0030346 A1* | 1/2009 | Kojima et al. .................. 600/590 |
| 2009/0187124 A1* | 7/2009 | Ludlow et al. .................. 601/47 |
| 2009/0227908 A1* | 9/2009 | Chau et al. ..................... 600/595 |

FOREIGN PATENT DOCUMENTS

| EP | 1787582 | 5/2007 |
| JP | 9-248282 | 9/1997 |
| JP | 2005-304890 | 11/2005 |
| JP | 2006-095264 | 4/2006 |
| WO | WO 2006013797 A1 * | 2/2006 |

OTHER PUBLICATIONS

European Search Report Dated Jun. 25, 2009.
"Analysis of Beer Drinking Motion Using Swallowing Function Evaluation System SFN-1" by S. Fujita, et al, May 2006 as shown on p. 12 of the document supplied by the applicant.

* cited by examiner

*Primary Examiner* — Max Hindenburg
*Assistant Examiner* — Michael C Stout
(74) *Attorney, Agent, or Firm* — Brundidge & Stanger, P.C.

(57) ABSTRACT

A living body inspection apparatus includes: a first detecting unit detecting a displacement of two positions in a lateral direction of a subject's larynx; a second detecting unit detecting a swallowing sound of the subject; a displaying unit displaying a waveform regarding the displacement of the two positions formed using information from the first detecting unit and a waveform regarding the swallowing sound formed using information from the second detecting unit; a processor instructing the displaying unit; and a flexible holding member including a pair of sensor holding members having flexibility and provided with the first and second detecting units at one ends, and a mounting member integrally formed with the pair of sensor holding members at other ends to hold the sensor holding members, the other ends being made open so that the mounting member is mounted on and held by the subject's larynx.

16 Claims, 11 Drawing Sheets

FIG. 8
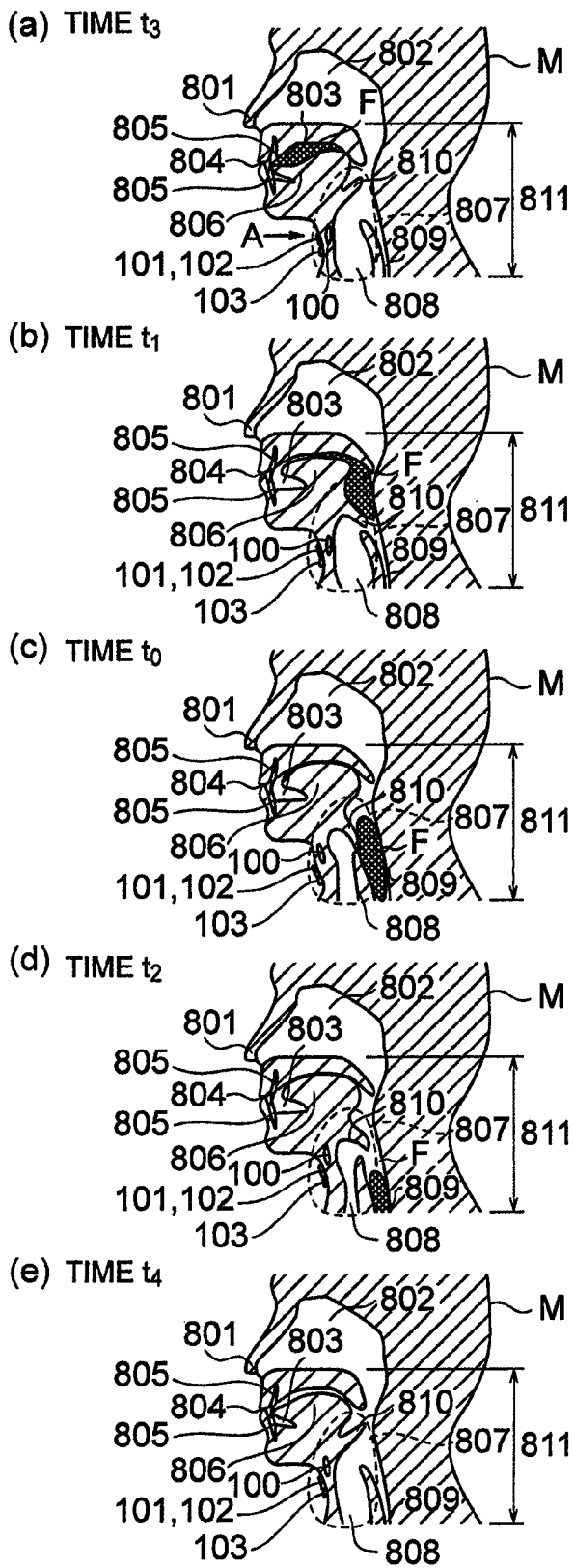
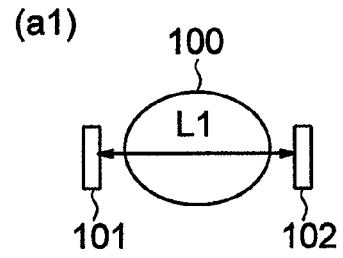
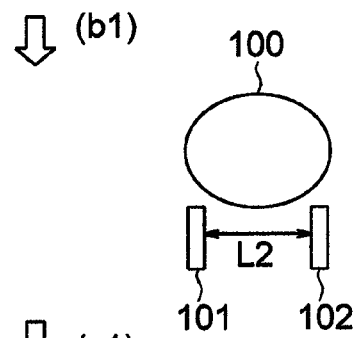
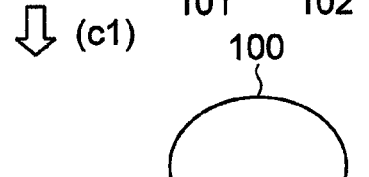
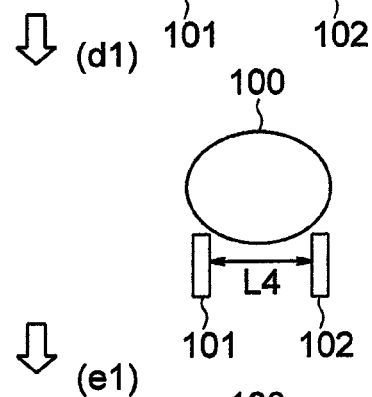
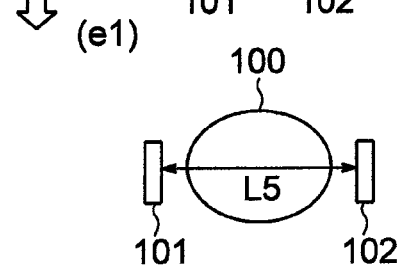

LIVING BODY INSPECTION APPARATUS

INCORPORATION BY REFERENCE

The present application claims priority from Japanese patent application JP2008-058917 filed on Mar. 10, 2008, the content of which is hereby incorporated by reference into this application.

BACKGROUND OF THE INVENTION

The present invention relates to a living body inspection apparatus for inspecting swallowing by a living body (an operation of transporting an alimentary bolus to be swallowed, from an oral cavity to a stomach).

Dysphagia is developed by degraded kinetic functions caused by advanced age, stroke such as brain infarct, cranial nerve degeneration disease (such as perkinsonism), and the like. In rapidly aging advanced countries, including Japan, dysphagia is found clinically frequently. Under dysphagia, an alimentary bolus may enter a bronchial tube (air passage), lung or the like, and pneumonia or the like, and it causes high temperature. Many cases have been recognized in which elderly persons having weakened body strength face a crisis of life.

Under these circumstances, a videofluoroscopic examination of swallowing (VF) is used most commonly as a method of correctly evaluating and grasping dysphagia. VF requires an X-ray radiographic apparatus in order to grasp a swallowing state, and a test subject swallows imaging agent such as barium sulfate to monitor a motion of alimentary bolus. A swallowing operation is constituted of a series of rapid motions, and these motions are likely to be missed if an X-ray radiographic apparatus only is used. Therefore, it is general that rapid motions are recorded in a video player for evaluations. However, VF is an examination having a possibility of aspiration, choke or the like, and careful attention is required. Furthermore, since an X-ray radiographic apparatus of a large size is required, there arise problems of radioactive exposure, time restrictions, cost and the like.

Another method used in recent years is a method of evaluating dysphagia with an endoscope using a fiber scope. This method is called a videoendoscopic examination of swallowing (VE). As compared to VF, VE has the advantages that the apparatus can be transported easily to a bed side or the like for examination, and evaluation is possible for the state of mucous membranes and tissues of a pharynx and larynx, for retained saliva and for others. However, a test subject feels uncomfortable when a fiber is inserted into a nasal cavity, and measurements are not simple because a fiber scope apparatus is required. From these reasons, VE is not still used widely. Further, at the climax of swallowing when an alimentary bolus enters the pharynx, a pharynx wall closes and a space in the pharynx is crushed. There arises therefore a problem that a view field of the endoscope becomes unclear, and observation cannot be made during the time period while the swallowing organ moves most frequently in a short time. This time period is called "whiteout" indicating a limit of VE examination.

As an approach to solving the problems associated with VF and VE, JP-A-2005-304890 (Patent Document 1) proposes a method of simply and accurately detecting dysphagia without burden on a patient. This approach by Patent Document 1 is characterized in that electrodes are attached to the surfaces of muscles associated with swallowing to record a surface electromyogram, that a microphone is used for recording swallowing sounds, that an acceleration sensor is used for recording vibrations while the larynx is raised, and that the acquired data is subjected to a neural network learning process to discriminate dysphagia.

According to Patent Document 1, however, it is necessary to form a database of the electromyogram, swallowing sounds and acceleration sensor data regarding the dysphagia, and to perform a neural network pattern learning. It takes, therefore, labor and time. Further, Patent Document 1 does not describe at all a discrimination method for healthy person so that operability is insufficient. Furthermore, without considering a relation between measured data, individual parameters are used for pattern learning to output only a discrimination result. It is therefore impossible to represent the degree of dysphagia by a visual representation. As above, Patent Document 1 does not describe at all how waveforms of measured data are compared, how the degree of dysphagia is directly judged from waveforms or the like, and means for simple judgment. Visual representation is therefore insufficient, and the degree of dysphagia and the like are difficult to be grasped crinically.

"Analysis of Beer Drinking Motion using Swallowing function evaluation system SFN-1" by Shohei FUJITA and five others, IEICE Technical Report MBE2006-7(2006-5), The Institute of Electronics, Information and Communication Engineers, May 2006, pp. 25-28 (Non-Patent Document 1) and JP-A-2006-95264 (Patent Document 2) propose a swallowing function evaluation system utilizing a pressure sensor (for detecting a larynx motion), a surface electromyogram and a vibration pickup (for detecting swallowing sounds). However, similar to Patent Document 1, Non-Patent Document 1 independently evaluates the parameters of each measured data (a cumulative value of an electromyogram, a time when an output of the pressure sensor becomes largest, an average period, a swallowing sound power), and does not describe at all how waveforms of measured data are compared, how the degree of dysphagia is directly judged from waveforms or the like, and means for simple judgment. Visual representation is therefore insufficient, and the degree of dysphagia and the like are difficult to be grasped crinically.

Non-Patent Document 1 proposes a measuring method by which four pressure sensors are disposed on a front surface of a thyroid cartilage at a pitch of 8 mm, and a sensor box fixing each pressure sensor is fixed to the neck by wounding a magic tape (registered trademark) around the neck. However, the four pressure sensors at spaced positions are insufficient for monitoring a continuous motion in an up/down direction of the thyroid cartilage. This arrangement provides only a precision sufficient for detecting a swallowing motion period, and it is also a demerit that the measuring method by wounding the magic tape (registered trademark) has strong obstructive nature and a test subject feels uncomfortable. The disclosure contents of Non-Patent Document 1 and Patent Document 2 do not disclose at all how waveforms of measured data are compared, how the degree of dysphagia is directly judged from waveforms or the like, and means for simple judgment. Visual representation is therefore insufficient, and the degree of dysphagia and the like are difficult to be grasped crinically.

Patent Document 1, Patent Document 2 and Non-Patent Document 1 disclose the methods basically using an electromyogram. However, since the methods using the electromyogram require a ground electrode and an earth electrode as described in Non-Patent Document 1, the number of electrodes increases, and handling the electrodes becomes complicated. Further, as described in Patent Document 1, since the larynx has four muscles (a geniohyoid muscle, a thyrohyoid muscle, a sternohyoid muscle, and a sternomastoid muscle), the method using an electromyogram has a demerit that the measurement results may differ unless the electrodes are disposed at correct positions of the larynx. This demerit exists always when an electromyogram is used. When a patient or novice nurse takes an electromyogram, the electrodes cannot be disposed correctly or handled properly. If disposable electrodes are used, there arises another problem of cost.

JP-A-9-248282 (Patent Document 3) discloses a method of detecting organism signals generated at a throat by mounting two acceleration sensors on an elastic stripe. This method aims at detecting voice signals, pulse signals and the like. Although this method detects mainly swallowing sounds, signals representative of a throat motion enter slightly. It is difficult to separate these signals and to use this method for dysphagia evaluation.

SUMMARY OF THE INVENTION

As described above, the apparatus for commonly used VF or VE becomes large, and a measuring person is required to have a high level of proficiency. It is therefore not possible that every person can measure easily at a bed side. Further, since the methods described in Patent Document 1, Patent Document 2 and Non-Patent document 1 use an electromyogram, the problems of electrode aligning and handling remain, and it is not possible that every person can measure easily at a bed side. Furthermore, the methods described in Patent Document 1 and Non-Patent Document 1 independently analyze a plurality of measured data sets, and do not disclose an analysis and display method for a plurality of measured data sets.

The present invention is made in view of these problems, and has an object to provide a living body inspection apparatus capable of inspecting easily dysphagia (or swallowing motion) and displaying the inspection results. It is also an object to facilitate mounting a sensor unit on a neck and reducing an influence of a size of a neck upon a measurement error.

A living body inspection apparatus of the present invention includes: larynx displacement detecting means for detecting a displacement of two positions in a lateral direction of a larynx of a test subject; swallowing sound detecting means for detecting a swallowing sound generated when the test subject swallows; displaying means; and processing means for instructing the displaying means to display a waveform regarding the displacement of two positions of the larynx and formed in accordance with information obtained from the larynx displacement detecting means and a waveform regarding the swallowing sound and formed in accordance with information obtained from the swallowing sound detecting means.

A flexible holding member of the living body inspection apparatus of the present invention has a discrete structural body constituted of a pair of sensor holding members and a neck mounting member. The neck mounting member is integrally formed with the pair of sensor holding members at one ends to hold the pair of sensor holding members and to be mounted on and held by the larynx of the test subject with the one ends being made open. The larynx displacement detecting means and swallowing sound detecting means are fixed to other ends of the sensor holding members. The one ends of the sensor holding members being integrally formed with opposite ends of the neck mounting member to follow a motion of a thyroid cartilage and the like. The sensor holding members are disposed inner than the neck mounting member, and opposite ends of the neck mounting member and the one ends of the sensor holding members are integrally coupled.

According to the living body inspection apparatus of the present invention, dysphagia can be inspected easily and the inspection results can be displayed. A flexible holding member has a discrete structural body constituted of a pair of sensor holding members and a neck mounting member. The neck mounting member is integrally formed with the pair of sensor holding members at one ends to hold the pair of sensor holding members and to be mounted on and held by the larynx of the test subject, the one ends being made open. The sensors disposed at the other end portions of the sensor holding members can be mounted always at generally the same positions on the larynx independently form the size of a neck. At the same time, the flexible holding member can be mounted from the front side of a neck (on the side of thyroid cartilage) so that mounding and dismounting the flexible holding member are easy. Further, not only the flexible holding member can be easily mounted and dismounted, but also the flexible holding member can be fixed always at generally the same position. Furthermore, since the flexible holding member is compact and light, it can be mounted for a long period of time, and long time continuous monitor of getting a meal or the like can be performed.

Other objects, features and advantages of the invention will become apparent from the following description of the embodiments of the invention taken in conjunction with the accompanying drawings.

Other objects, features and advantages of the invention will become apparent from the following description of the embodiments of the invention taken in conjunction with the accompanying drawings.

BRIEF DESCRIPTION OF THE DRAWINGS

FIG. 4A is for a healthy person, FIG. 4B is for a dysphagia patient of a slight degree, and FIG. 4C is for a dysphagia patient of a middle degree.

FIG. 8, (a) to (e) are diagrams illustrating the states of a body of a test subject during swallowing, and FIG. 8, (a1) to (e1) are schematic diagrams illustrating distances between an oscillation coil and a detection coil.

DETAILED DESCRIPTION OF THE EMBODIMENTS

A time period of swallowing is roughly divided into three time periods, an oral cavity period, a pharynx period and an esophagus period. The oral cavity period is a time period while an alimentary bolus is transported from the oral cavity to the pharynx. The pharynx period is a time period while the alimentary bolus is transported from the pharynx to the esophagus upon induction of a swallowing reflex. The esophagus period is a time period while the alimentary bolus is transported from the esophagus to the stomach. The present invention provides a living body inspection apparatus regarding dysphagia during the oral cavity period and pharynx period. A swallowing operation of a test subject M described in the following is preferably performed by swallowing live saliva, a small amount of water or the like.

With reference to the accompanying drawings, detailed description will be made on best modes for carrying out the present invention (hereinafter called embodiments).

Figure 1:
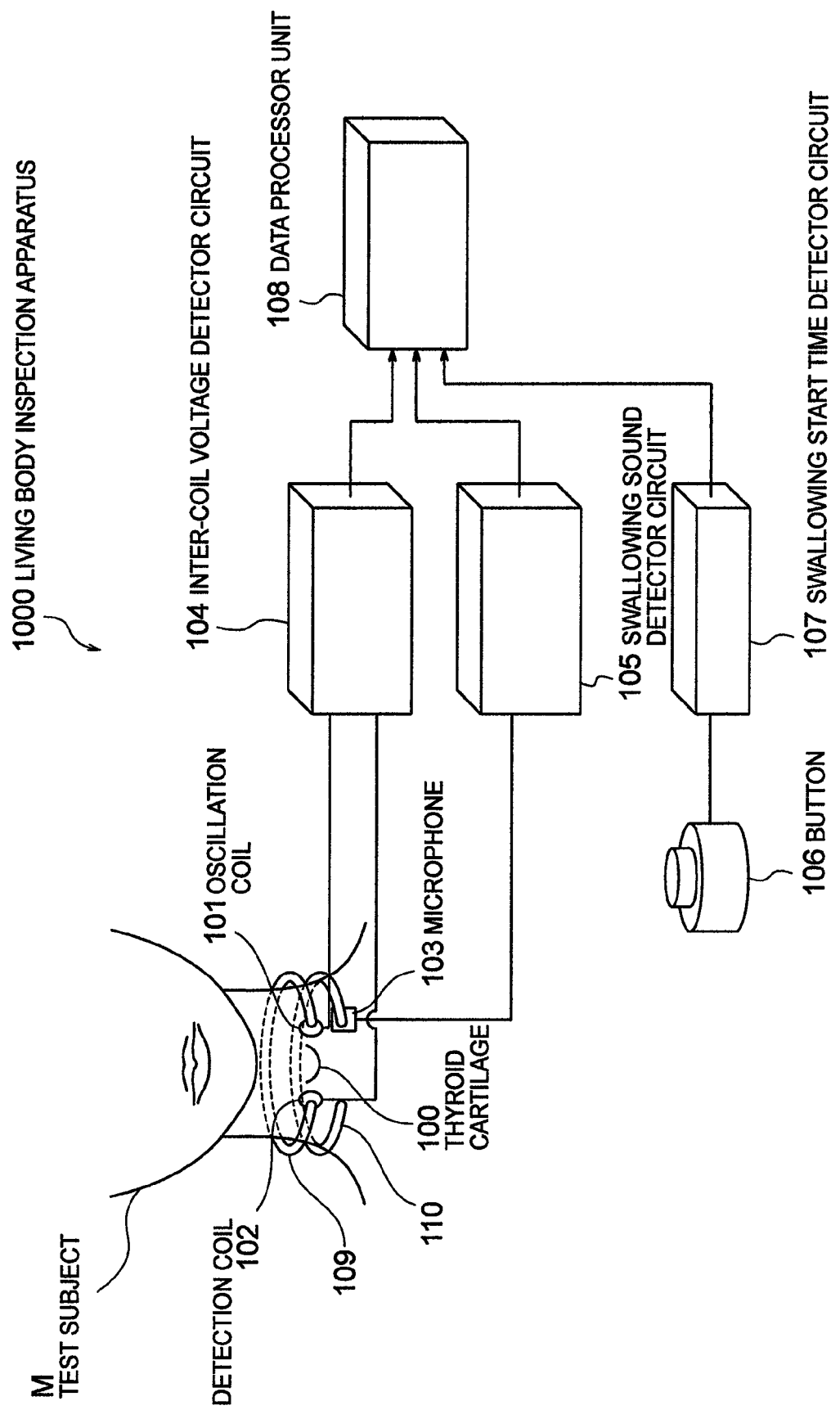
FIG. 1 is a diagram illustrating an example of the structure of a living body inspection apparatus according to an embodiment.

FIG. 1 is a diagram illustrating an example of the structure of a living body inspection apparatus according to an embodiment of the invention.

As illustrated in FIG. 1, a living body inspection apparatus 1000 has an oscillation coil 101 (larynx displacement detecting means) and a detection coil 102 (larynx displacement detecting means) respectively held by a flexible holding member 109 (holding means) and disposed on both sides of a thyroid cartilage 100 (popularly known as an Adam's apple) of a test subject M. The oscillation coil 101 and detection coil 102 are connected to an inter-coil voltage detector circuit 104, and an output of the inter-coil voltage detector circuit is input to a data processor unit 108. A microphone 103 (swallowing sound detecting means) held by a flexible holding member 110 (holding means) is disposed near the thyroid cartilage 100. The microphone 103 is preferably a microphone using a piezoelectric element because surrounding sounds other than swallowing sounds are difficult to be picked up. However, a condenser type microphone may also be used. The microphone 103 is connected to a swallowing sound detector circuit 105 to be supplied with a power source and the like for the operation thereof. The swallowing sound detector circuit 105 outputs a voltage representative of a detected swallowing sound which voltage is input to the data processor unit 108. The flexible holding member used in the embodiment will be detailed later with reference to FIG. 3, FIGS. 9A and 9B and FIG. 10.

The living body inspection apparatus 1000 illustrated in FIG. 1 is further provided with a button 106 (operating means) (or a switch) for detecting a swallowing start time. The button 106 is connected to a swallowing start time detector circuit 107 for detecting a trigger signal representative of a start time entered from the button. The swallowing start time detector circuit 107 delivers an output signal, for example, by generating and outputting a clock waveform and generating and outputting a trigger signal of a digital signal level. An output voltage from the swallowing start time detector circuit 107 is input to the data processor unit 108, and is used as a trigger signal of data fetch by the data processor unit 108.

A work of depressing the button 106 is performed by a medical doctor or a nurse or directly by a patient. By using a time when the button 106 is depressed as an initial time (swallowing start time), the data processor unit 108 detects a swallowing sound peak time from an output voltage of the swallowing sound detector circuit 105. Next, by using the swallowing sound peak time as a reference, the data processor unit 108 detects a peak time of a waveform detected by the inter-coil voltage detector circuit 104, and detects and analyzes two-phase properties of a waveform. The details of judgment and analysis processes by the data processor unit 108 will be later described.

Figure 3:
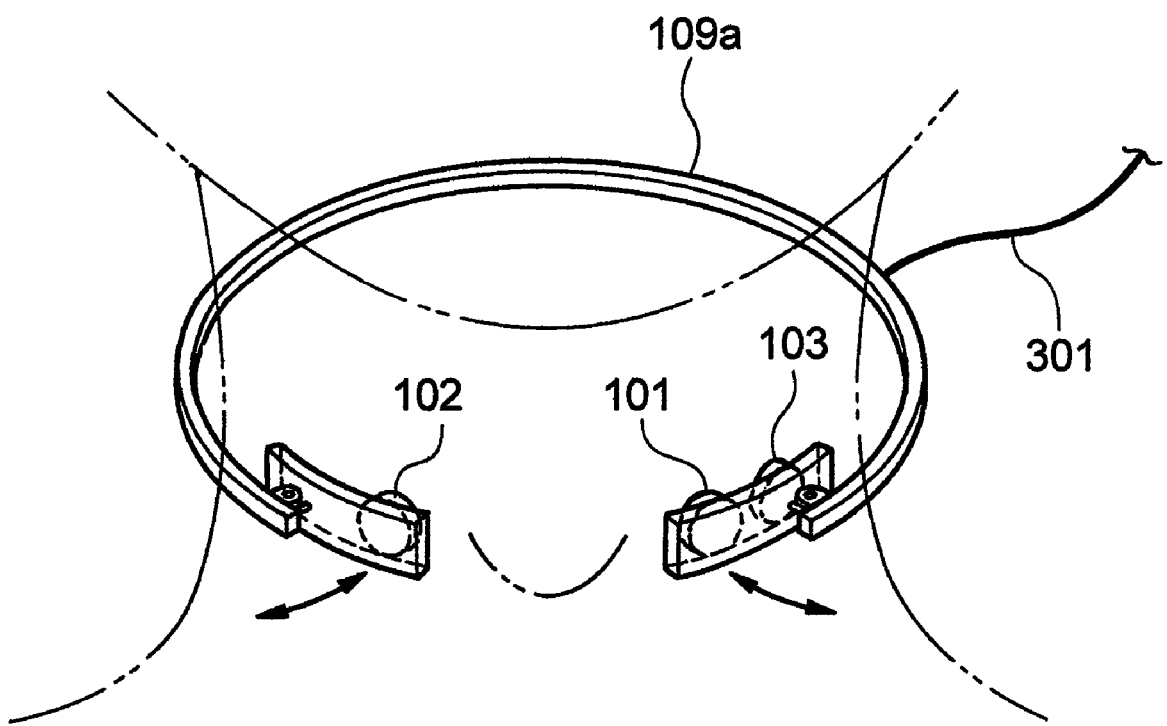
FIG. 3 is a diagram illustrating an embodiment of a flexible holding member.

The oscillation coil 101, detection coil 102 and microphone 103 illustrated in FIG. 1 may be held by one flexible holding member 109a as illustrated in FIG. 3. In the example illustrated in FIG. 3, the oscillation coil 101 and detection coil 102 are disposed at positions nearer to each other along the circumference of the flexible holding member 109a, and the microphone 103 is disposed on the side opposite to the detection coil 102 or the oscillation coil 101. The distance between the oscillation coil 101 and detection coil 102 is set as short as possible in order to detect a change in a weak magnetic field intensity at a high detection sensitivity. As the oscillation coil 101 and detection coil 102 are mounted on the flexible holding member 109 or 109a in this manner, it becomes possible to suppress vibrations of a skin of the larynx (near the thyroid cartilage 100) and pick up a fine change of the larynx (a displacement at a maximum level of several mm) at high precision. The material of the flexible holding members 109, 110 and 109a may be any type of resin or the like if the material has flexibility.

Figure 9A:
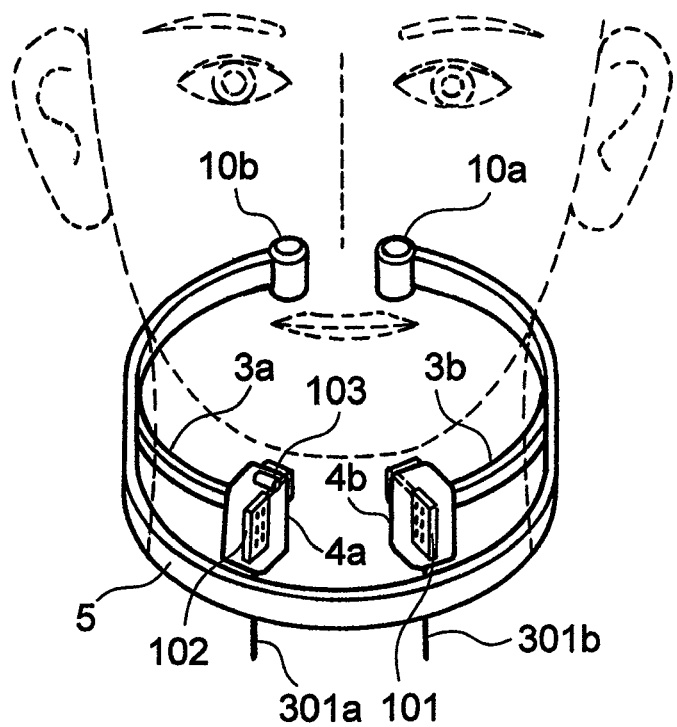
FIGS. 9A and 9B are diagrams illustrating a flexible holding member according to another embodiment.
Figure 9B:
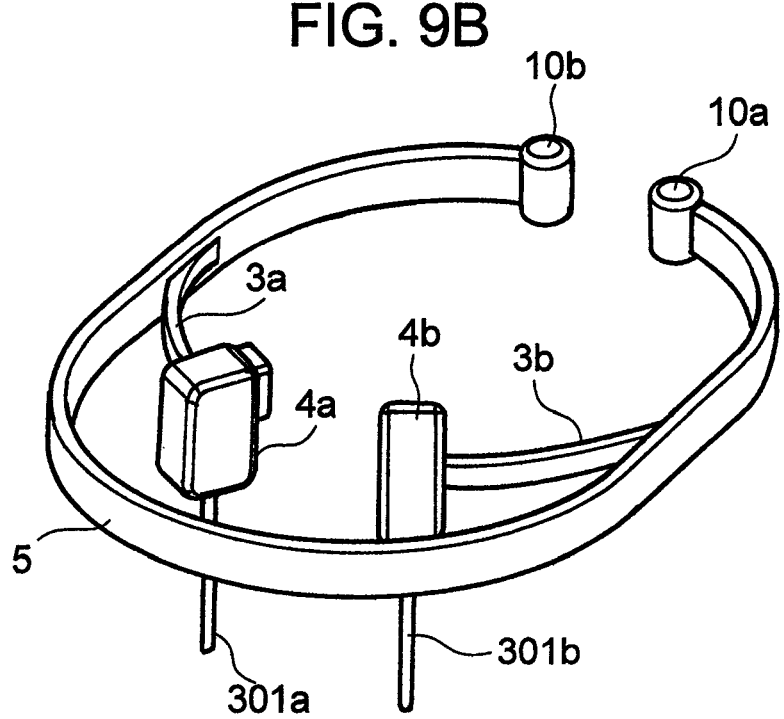

FIGS. 9A and 9B illustrate the details of a flexible holding member according to another embodiment. FIG. 9B is a perspective view of FIG. 9A. This flexible holding member has a discrete structural body constituted of a pair of sensor holding members 3a and 3b and a neck mounting member 5. With this structural body, the neck mounting member 5 is integrally formed with one end portions of the pair of sensor holding members 3a and 3b, and the other end portions are made open for mounting the flexible holding member on the larynx of a test subject. Sensors 4a and 4b are disposed at other end portions of the pair of sensor holding members 3a and 3b. The larynx displacement detecting means (e.g., oscillation coil 101 or detection coil 102) and swallowing sound detecting means (e.g., microphone 103) are fixed in the sensors 4a and 4b. The one end portions of the sensor holding members 3a and 3b are integrally formed with opposite end portions of the neck mounting member 5 to thereby provide an open structure capable of flexing to follow a motion of thyroid cartilage 100 and the like. The pair of sensor holding members 3a and 3b are disposed inner than the neck mounting member 5, and the opposite end portions of the neck mounting member and one end portions of the sensor holding members are formed integrally. The sensor holding members 3a and 3b can be mounted without contacting the neck, and has a structure capable of following a swallowing motion independently from the neck mounting member 5. An oscillation coil 101, a detection coil 102 and a microphone 103 are disposed at other ends of the pair of sensor holding members 3a and 3b. In this embodiment in particular, the oscillation coil 101 and detection coil 102 are disposed at the other ends of the pair of sensor holding members 3a and 3b in such a manner that the two coils face each other (near along a vertical direction of the neck surface), allowing a high signal to noise (S/N) ratio. It is possible, therefore, to dispose the microphone 103 along a direction generally perpendicular to the direction of the oscillation coil 101 and detection coil 102. An amount of magnetic field noises generated by the microphone 103 and mixed with the oscillation coil and/or detection coil can therefore be reduced. The mutual positions of the oscillation coil and detection coil and the position of the microphone in a perpendicular relation are not limited, but other positions may be set if a sufficiently high S/N ratio is ensured. Neck abutting portions 10a and 10b having a cylindrical shape, a spherical shape or the like are formed at two opposite end portions (portions of the neck rear side) of the neck mounting member 5. Mounting becomes easy independently from the size of a neck, because of four abutting portions including the two abutting portions and two sensor portions disposed at the other end portions of the sensor holding members. The sensors built in the sensor portions 4a and 4b are connected to the inter-coil voltage detector circuit 104 and swallowing sound detector circuit 105 via wirings 301a and 301b.

Figure 10:
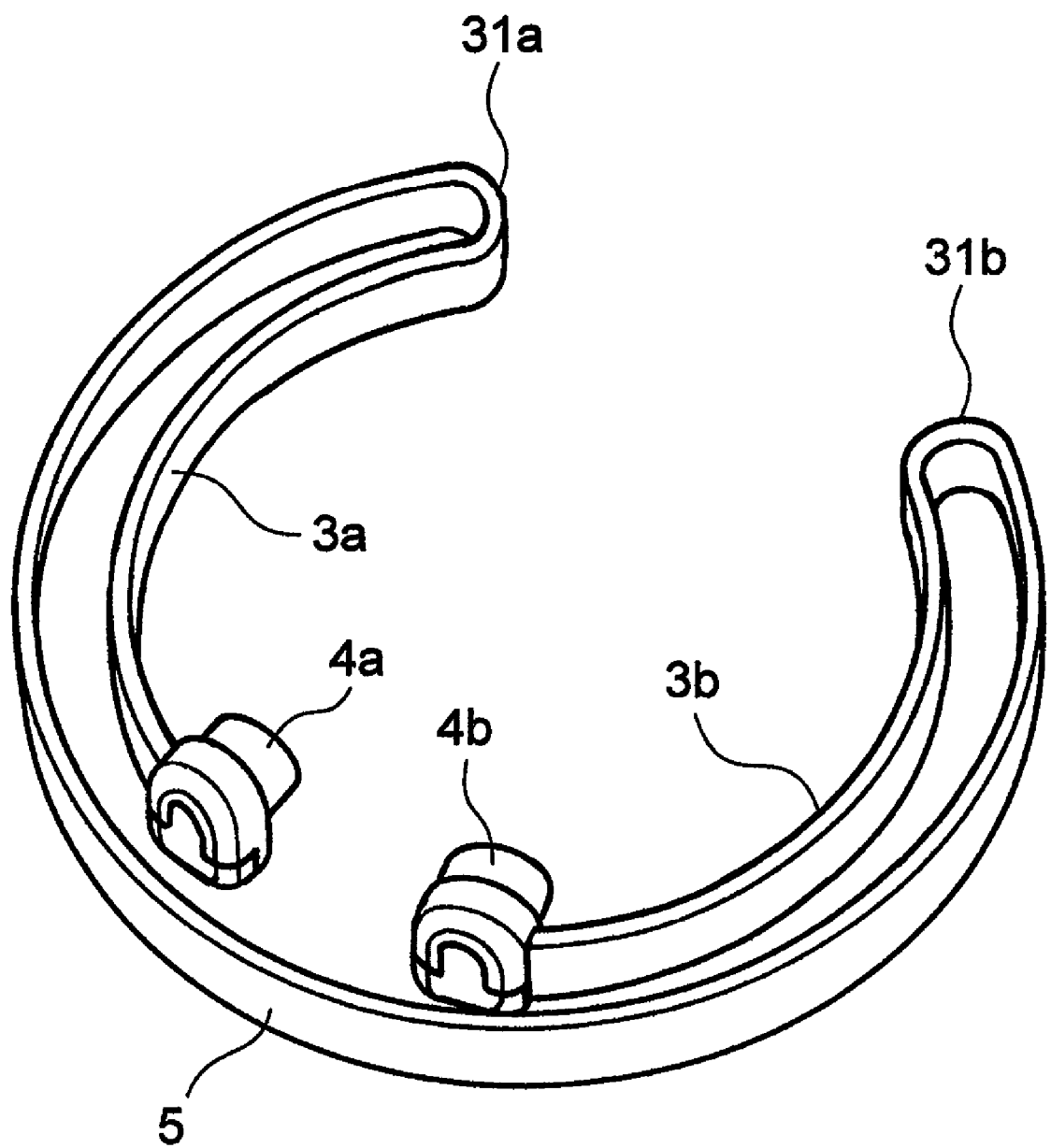
FIG. 10 is a diagram illustrating a flexible holding member according to another embodiment.

FIG. 10 illustrates a flexible holding member according to still another embodiment. Similar to the embodiment illustrated in FIGS. 9A and 9B, the flexible holding member illustrated in FIG. 10 has a discrete structural body constituted of a pair of sensor holding members 3a and 3b and a neck mounting member 5. With this structural body, the neck mounting member 5 is integrally formed with one end portions of the pair of sensor holding members 3a and 3b at flexed portions 31a and 31b, and the end portions are made open for mounting the flexible holding member on the larynx of a test subject. Sensors 4a and 4b are disposed at other end portions of the pair of sensor holding members 3a and 3b. The larynx displacement detecting means (e.g., oscillation coil 101 or detection coil 102) and swallowing sound detecting means (e.g., microphone 103) are fixed in the sensors 4a and 4b. The one end portions of the sensor holding members 3a and 3b are integrally formed with opposite end portions of the neck mounting member 5 to thereby provide an open structure capable of flexing to follow a motion of thyroid cartilage and the like. The mutual positions of the oscillation coil and detection coil and the position of the microphone in a perpendicular relation, respectively in the sensor portions 4a and 4b are determined in such a manner that a sufficiently high S/N ratio is ensured.

By making the flexible holding member have the discrete structural body constituted of the pair of sensor holding members and the neck mounting member, the sensors disposed at the other end portions of the sensor holding members can be mounted always at generally the same positions on the larynx independently form the size of a neck. At the same time, the flexible holding member of the embodiments can be mounted from the front side of a neck (on the side of thyroid cartilage) so that mounding and dismounting the flexible holding member are easy. Further, not only the flexible holding member can be easily mounted and dismounted, but also the flexible holding member can be fixed always at generally the same position. Furthermore, since the flexible holding member is compact and light, it can be mounted for a long period of time, and long time continuous monitor of getting a meal or the like can be performed.

Figure 11:
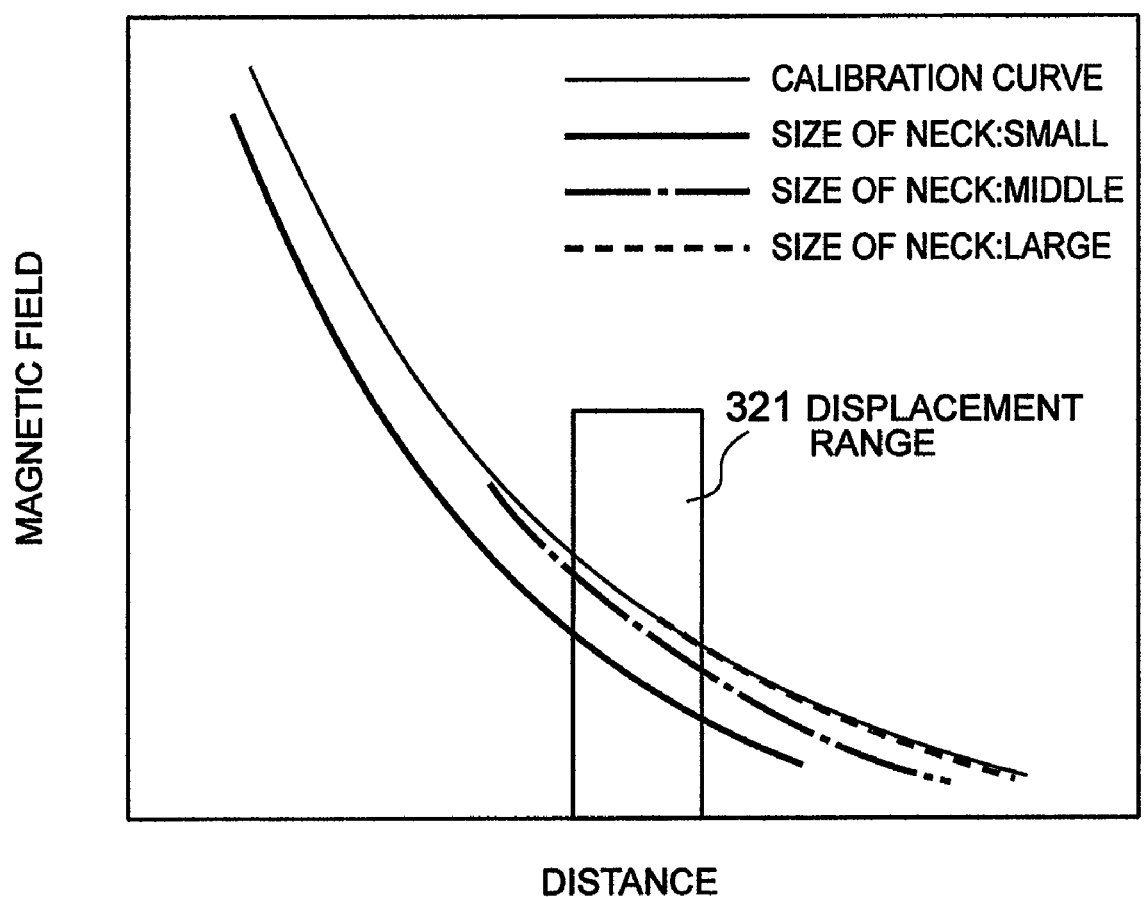
FIG. 11 is a diagram illustrating a relation between a magnetic field and a distance.

By using the flexible holding member of the embodiments, the sensors can be disposed at generally the same positions independently from the size of a neck of a test subject. It is therefore easy to convert a voltage into a distance change amount. FIG. 11 illustrates a relation between a magnetic field (or measured voltage) and a distance obtained by using the oscillation coil 101 and detection coil 102. As illustrated in FIG. 11, it can be understood that there is a tendency that as the size of a neck becomes large, a magnetic filed intensity becomes small. However, it can be understood further that a gradient of a magnetic field—distance curve is generally constant in a displacement range 321 at any size of a neck. Namely, with a mounting method of the embodiment, a motion (change amount) in the displacement range can be detected. Therefore, a measured magnetic filed (or measured voltage) is converted into a distance by using a calibration curve. In calculating an actual motion (change amount), a distance at an initial point when the flexible holding member is mounted is used as a bias value (initial value), and the bias value is subtracted from a converted distance measured at a different time so that a distance (change amount) moved from the initial value can be detected correctly.

Next, with reference to FIG. 2, detailed description will be made on the overall structure of the living body inspection apparatus illustrated in FIG. 1 (refer also FIG. 1 when necessary). The data processor unit 108 is constituted of a processor 1081 (processing means) such as a central processing unit (CPU), a storage unit 1082 such as a random access memory (RAM), a read only memory (ROM) and a hard disk drive (HDD), an input unit 1083 such as a keyboard, a display unit (displaying means) 1084 such as a liquid crystal display.

In the living body inspection apparatus 1000, an AC generator circuit 206 generates an AC voltage having a predetermined frequency (e.g., 20 kHz). The generated AC voltage having the predetermined frequency is converted into an AC current having the predetermined frequency by a current generator amplifier circuit 207. The AC current flows through the oscillation coil 101 mounted on a living body.

A magnetic field generated by the oscillation coil 101 generates an induced electromotive force in the detection coil 102 mounted on the living body. The generated induced electromotive force (having the same frequency as that of the AC voltage having the predetermined frequency generated by the AC generator circuit 206) is amplified by a preamplifier circuit 201 (amplifier circuit). The amplifier signal is input to a detector circuit 202. The detector circuit 202 detects the signal by using the predetermined frequency of the AC voltage generated by the AC generator circuit 206, or by using a two-fold frequency of the predetermined frequency. To this end, a phase of an output of the AC generator circuit 206 is adjusted by a phase adjustor circuit 208, and then the phase adjusted signal is input as a reference signal c to a reference signal input terminal (now shown) of the detector circuit 202.

If detection is performed at a two-fold frequency of the predetermined frequency, the phase adjuster circuit 208 is not necessarily required. In a simple circuit arrangement for two-fold frequency detection, the predetermined frequency of the AC generator circuit 206 is set to the two-fold frequency, and this two-fold frequency is converted into a half frequency by a frequency divider and thereafter input to the current generator amplifier 207. As the reference signal c, a signal having the two-fold frequency of the predetermined frequency of the AC generator circuit 206 is input to the reference signal input terminal of the detector circuit. If there is no fear of interference, a full wave rectifier circuit may be used in place of the detector circuit. This detection is generally called an envelope detection.

An output of the detector circuit 202 is passed through a low-pass filter (LPF) circuit 203 having a cut-off frequency of, e.g., 10 Hz, and amplified by an amplifier circuit 204 to obtain an output 205 of a desired voltage. Lastly, the output 205 is input to the data processor unit 108 as digital data converted by a built-in analog digital conversion board (AD board, not shown). In this case, a DC bias voltage of the output 205 is removed by an offset adjustor circuit 215 at the front of the amplifier circuit 204. This DC bias voltage appears depending upon initial setting positions of the oscillation coil 101 and detection coil 102 (because of a difference of the size of a neck of each test subject M). As a method of removing the DC bias voltage, the DC bias voltage is once read to the data processor unit 108, and the data processor unit 108 performs digital analog conversion (DA conversion) so as to make the bias voltage have 0 voltage. As another simple method, the DC bias voltage may be removed a high-pass filter.

Figure 2:
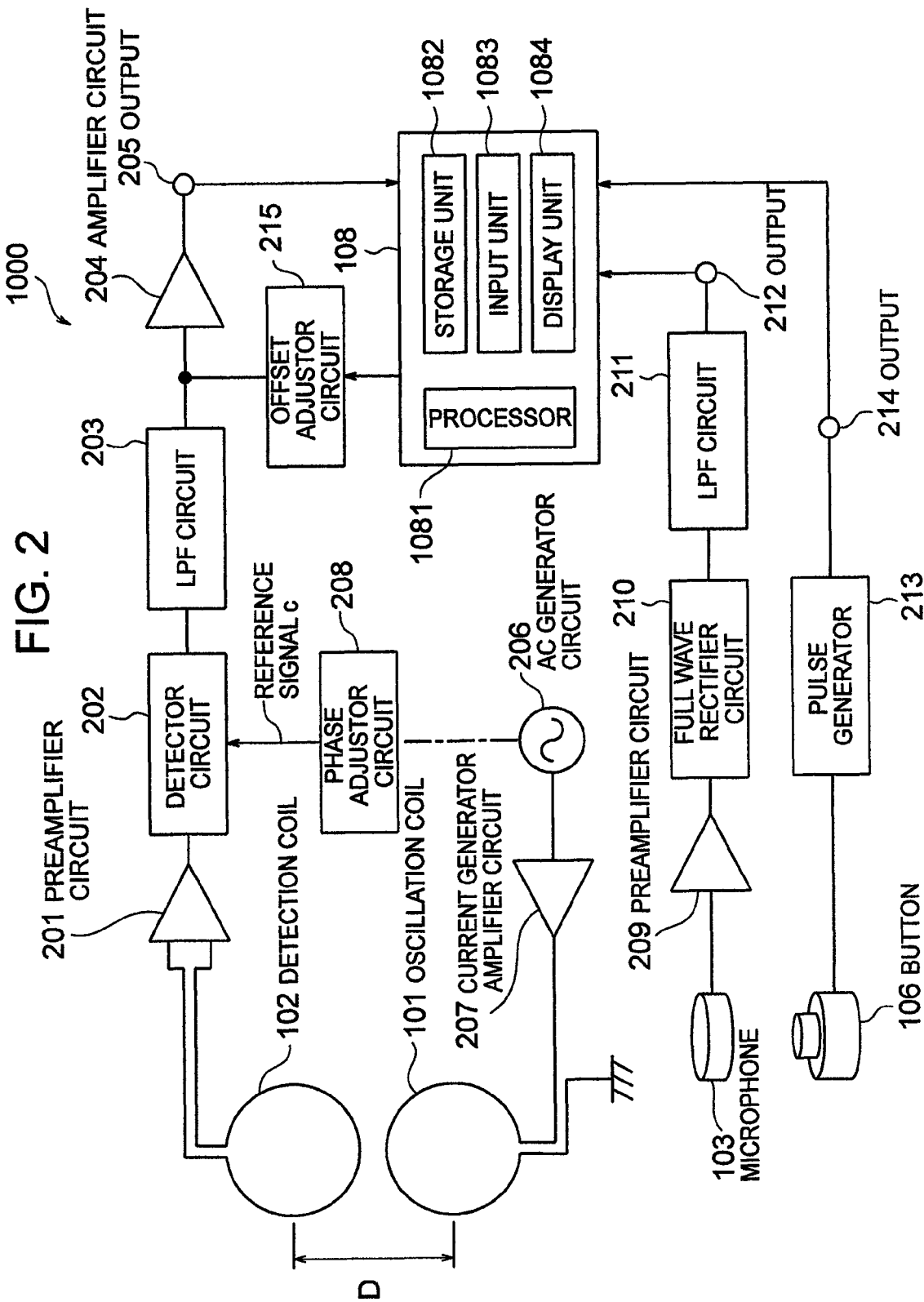
FIG. 2 is the detailed illustrative diagram of an overall structure of the living body inspection apparatus of the embodiment.

The microphone 103 illustrated in FIG. 2 may have a power source therein or the power source may be supplied externally. An output voltage waveform of the microphone 103 has a signal band width of several ten kHz. A full wave rectifier circuit 210 (full wave rectifying means) converts a signal obtained from the microphone 103 via a preamplifier circuit 209 into a unidirectional signal (e.g., only positive voltage components). This signal is passed through an LPF circuit 211 (in this example, 10 Hz) so that only an envelope of a swallowing sound signal can be formed (envelope detection). A signal band width of the swallowing sound may be used directly. However, by using the envelope waveform formed by the full wave rectifier circuit 210 and LPF circuit 211, a signal having a band width not higher than 10 Hz can be formed so that measurement at a low sampling frequency of about 100 Hz is possible. Since the output signal 212 has a similar low frequency band (not higher than 30 Hz), the sampling frequencies for the whole living body inspection apparatus 1000 can be lowered, and an amount of measured data can be reduced advantageously.

The button 106 illustrated in FIG. 2 may be any type of a switch. In this case, an output 214 can be obtained by making a pulse generator 213 generate and output a clock waveform and a trigger signal. The button 106 and pulse generator 213 provide only a function of reading a swallowing start time. Therefore, the arrangement is not limited to the embodiment, but other arrangements may be incorporated such as wireless approach.

Figure 4A:
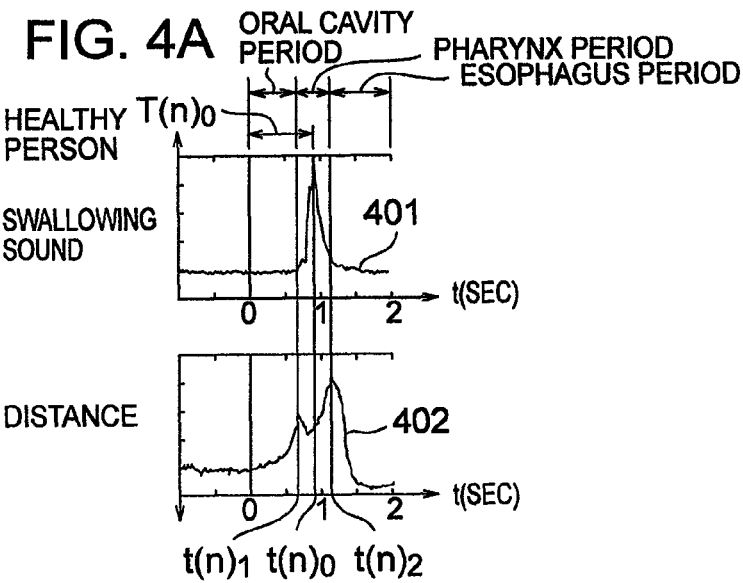
FIGS. 4A to 4C are diagrams illustrating swallowing voice waveforms and distance waveforms (inter-coil voltage waveforms)
Figure 4B:
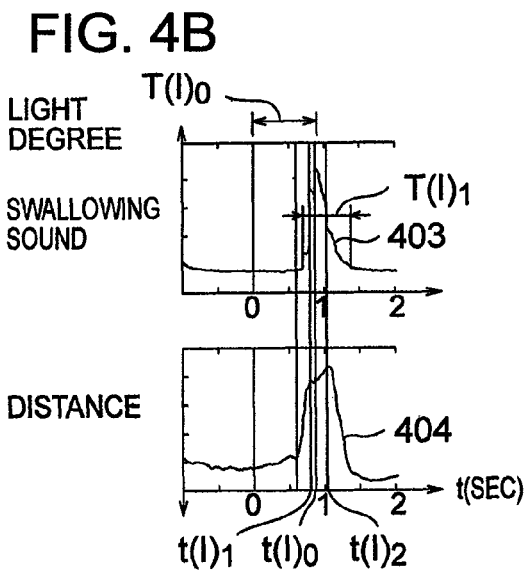
Figure 4C:
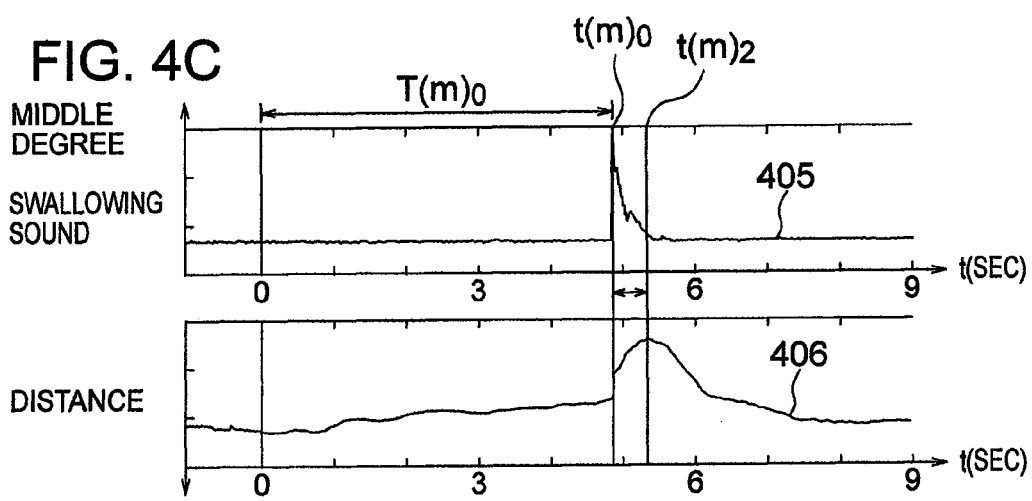

Examples of data of a healthy person and dysphagia persons measured with the living body inspection apparatus 1000 illustrated in FIGS. 1 and 2 are illustrated in FIGS. 4A to 4C (refer to other drawings when necessary). Examples of data illustrated in FIGS. 4A to 4C are displayed on the display unit 1084 of the data processor unit 108.

FIG. 4A illustrates a swallowing sound waveform 401 of a healthy person and a distance waveform (inter-coil voltage waveform) 402. FIG. 4B illustrates a swallowing sound waveform 403 of a dysphagia patient of a low degree and a distance waveform (inter-coil voltage waveform) 404. FIG. 4C illustrates a swallowing sound waveform 405 of a dysphagia patient of a middle degree and a distance waveform (inter-coil voltage waveform) 406. The values of the distance waveforms 402, 404 and 406 become large in this order.

In FIG. 4A, a time $t(n)_0$ is a peak (maximum) time of a swallowing sound. A time $t(n)_1$ is a minimum (peak) time of a distance before the swallowing sound peak time $t(n)_0$. A time $t(n)_2$ is a minimum (peak) time of a distance after the swallowing sound peak time $t(n)_0$. $T(n)_0$ represents a time width from a swallowing start time (0: a time when the button 106 is operated) to the swallowing sound peak time $t(n)_0$.

In this manner, a pattern of a healthy person indicates two peaks in the distance waveform 402. The oral cavity period, pharynx period and esophagus period of swallowing are illustrated in FIG. 4A.

In FIG. 4B, times $t(l)_0$, $t(l)_1$, $t(l)_2$ and a time width $T(l)_0$ are similar to the times $t(n)_0$, $t(n)_1$, $t(n)_2$ and time width $T(n)_0$ illustrated in FIG. 4A. However, the distance waveform 404 is different from the distance waveform 402 (details will be described later).

Further in FIG. 4C, times $t(m)_0$ and $t(m)_2$ are similar to the times $t(n)_0$ and $t(n)_2$ illustrated in FIG. 4A. However, the distance waveform 406 is considerably different from the distance waveform 402 in that there is no minimum value of the distance before the swallowing sound peak time $t(m)_0$ (details will be described later).

Namely, a concave shape forming two peaks on both sides of the swallowing sound peak time is recognized as a distance waveform of a healthy person (the cause of forming this concave shape will be later described with reference to FIG. 8).

On the other hand, it can be understood that the distance waveform of dysphagia is likely to form a single peak and that a definite maximum value is not present particularly at the swallowing sound peak time. It can also be understood from the swallowing sound waveform 405 and distance waveform 406 of the dysphagia patient of the middle degree that the time width $T(m)_0$ from the swallowing start time 0 to the swallowing peak time $t(m)_0$ prolongs and the transport operation of the alimentary bolus is delayed. It can also be understood from the distance waveform 406 that the time width from the swallowing peak time $t(m)_0$ to the time $t(m)_2$ prolongs.

As described above, by displaying the swallowing sound waveform and distance waveform at the same time, it is possible to see how the epiglottis (refer to FIG. 8) moves by checking the degree of swallowing time prolongation and whether the waveform has a single peak. It is possible to visually grasp the degree of dysphagia as a whole. By using the swallowing peak time as a reference, dysphagia can be grasped quantitatively from the time prolongation degree of epiglottis insufficiency and the like.

Figure 5:
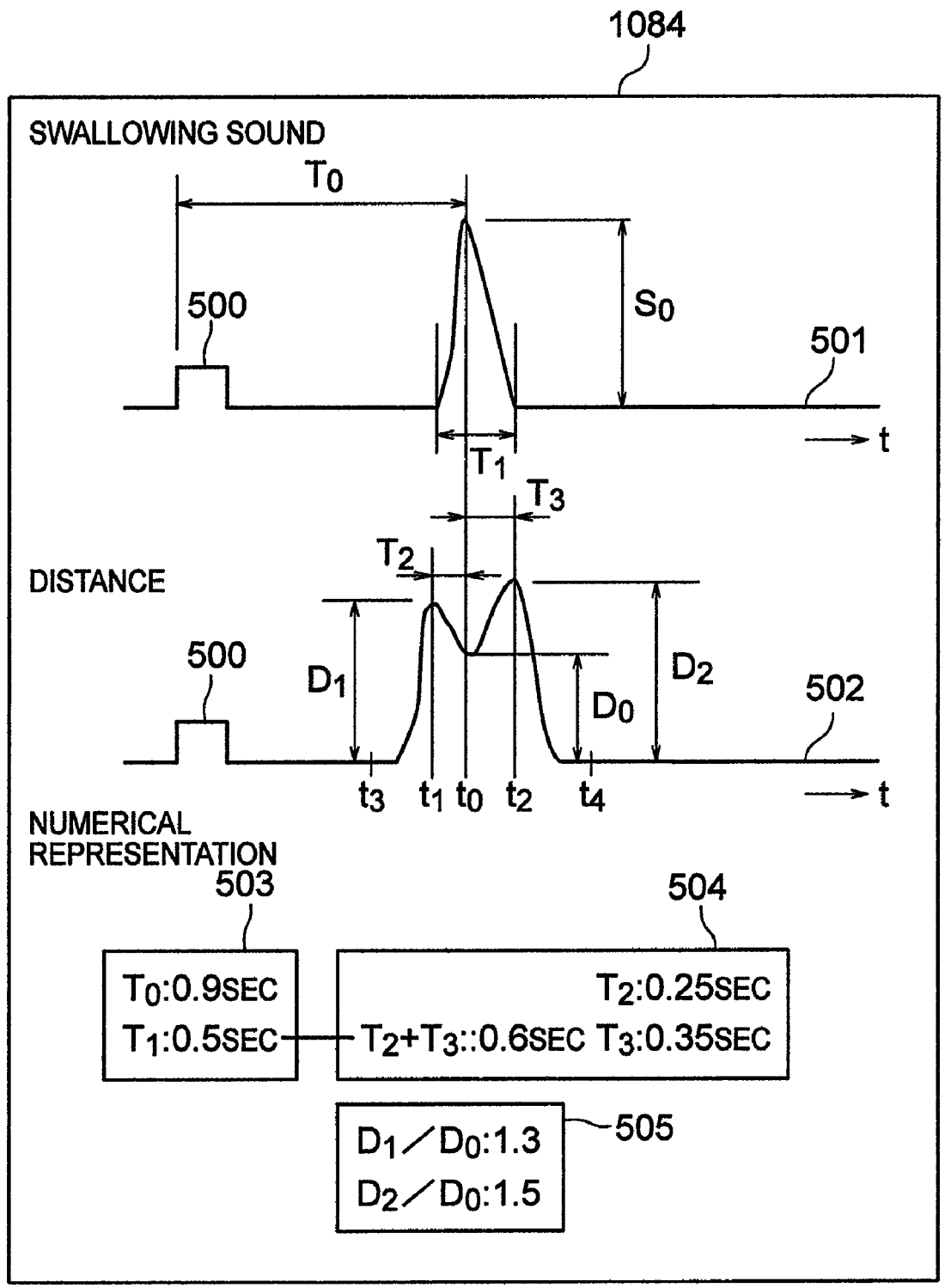
FIG. 5 is a diagram illustrating a waveform analyzing method for the living body inspection apparatus of the embodiment.

FIG. 5 is a diagram illustrating a waveform analysis method (refer to other drawings when necessary). This diagram is displayed on the display unit 1084 of the data processor unit 108, and each process and calculations are performed by the processor unit 1081.

In FIG. 5, in order to make visually easy to recognize a swallowing start, a swallowing start clock 500 at the time when the button 106 is operated is displayed on both a swallowing sound waveform 501 and a distance waveform (inter-coil voltage waveform) 502. A time width from the swallowing start clock 500 to a peak time of the swallowing sound waveform 501 is represented by $T_0$, and a swallowing sound peak time is represented by $t_0$. A sound intensity at the time $t_0$ is represented by $S_0$. By using the swallowing sound peak time $t_0$ as a reference, a time width $T_1$ from the start to end of a swallowing sound is detected. In automatically detecting this time width $T_1$, a half value (half width) of the sound intensity $S_0$ at the time $t_0$ may be used or a time when the amplitude becomes $S_0$ divided by an integer number (e.g., 1/10) may be used.

Automatically detected next are a voltage amplitude $D_0$ at time $t_0$, a voltage amplitude $D_1$ at a peak time $t_1$ before the time $t_0$, and a voltage amplitude $D_2$ at a peak time $t_2$ after the time $t_0$, respectively of the distance waveform 502. Also automatically detected are a time width $T_2$ between the times $t_1$ and $t_0$ and a time width $T_3$ between the times $t_0$ and $t_2$.

In order to visually display dysphagia in an easily understandable manner, a time parameter display area 503 for the swallowing sound waveform, a time parameter display area 504 for the distance waveform and a distance ratio parameter display area 505 are displayed on the same screen as that for the swallowing sound waveform 501 and distance waveform 502. A transport time of the alimentary bolus can be known from $T_0$ and $T_1$ displayed in the time parameter display area 503 for the swallowing sound waveform.

It is possible to judge whether the distance waveform has a single peak, to judge a delay of the epiglottis, or to judge other factors, from the value of $T_2$ or $T_3$ displayed in the time parameter display area 504 for the distance waveform. It is possible to judge from comparison between an addition value of $T_2$ and $T_3$ and the value of $T_1$ whether the time zone of closure of the epiglottis is approximately equal to the time while the alimentary bolus is transported. For example, in the example of dysphagia of the light degree illustrated in FIG. 4B, it can be understood from comparison between the swallowing sound waveform 403 and distance waveform 404 that the value of $T_1$ is longer than the addition value of $T_2$ and $T_3$.

As described above, the time parameter display area 503 for the swallowing sound waveform, time parameter display area 504 for the distance waveform and distance ratio parameter display area 505 are displayed at the same time when the swallowing sound waveform 501 and distance waveform 502 are displayed. It is therefore possible to easily, visually and quantitatively grasp dysphagia. It is also possible to display various parameters such as the time parameters and distance ratio parameters, on the swallowing waveform and distance waveform, by using auxiliary lines.

A flow of a method of detecting the time parameters ($t_0$, $t_1$, $t_2$, $T_0$, $T_1$, $T_2$, $T_3$), distance amplitudes ($D_0$, $D_1$ and $D_2$) and the swallowing sound maximum amplitude ($S_0$) illustrated in FIG. 5 will be described with reference to FIG. 6 (refer to other drawings when necessary). This detecting method and the like are executed by the processor 1081 of the data processor unit 108. The times $t_3$ and $t_4$ will be described later.

First, the processor 1081 displays the swallowing sound waveform and distance waveform (inter-coil voltage waveform) on the display unit 1084 (Step S601). By using the displayed waveforms, the processor 1081 detects the time ($t_0$) at the maximum swallowing sound amplitude after the swallowing start, from the swallowing sound waveform, and detects the maximum amplitude ($S_0$) at the time ($t_0$) (Step S602). Next, the processor 108 detects the swallowing sound continuation time width ($T_1$) by various methods such as detecting a half value (half width) of $S_0$, detecting the time when the amplitude becomes $S_0$ divided by an integer number (e.g., 1/10), and detecting the time when a set threshold value is crossed (Step S603).

Next, the processor 1081 uses a function of detecting a two-phase waveform of the distance waveform relative to the time ($t_0$), by detecting the difference time widths ($T_2$ and $T_3$) and the amplitudes ($D_1$ and $D_2$) at the times ($t_1$ and $t_2$) to detect the parameters regarding two-phase properties (Step 604). More specifically, the processor detects the time ($t_1$) when the amplitude of the distance waveform becomes maximum at the time before the time ($t_0$), to detect the amplitude ($D_1$) of the distance waveform at the time ($t_1$), and the time ($t_2$) when the amplitude of the distance waveform becomes maximum at the time after the time ($t_0$), to detect the amplitude ($D_2$) of the distance waveform at the time ($t_2$).

The processor 1081 calculates ratios such as $D_1/D_0$ and $D_2/D_0$ to clarify the relations of lengths of the distances of $D_0$, $D_1$, and $D_2$ (Step S605).

This ratio calculation can absorb individual differences of test subjects M and differences of mount positions, and can obtain correct values without converting inter-coil voltages representative of distance changes of several mm at the most into correct distances.

After the above-described processes, the processor 1081 can display various numerical values at the same time when the swallowing sound waveform and distance waveform are displayed (Step S606) (refer to FIG. 5).

After Step S606, the processor 1081 performs judgments of dysphagia and displays judgment results on the display unit 1084 (Step S607). This Step S607 will be described in detail with reference to FIG. 7 (refer to other drawings when necessary).

Figure 6:
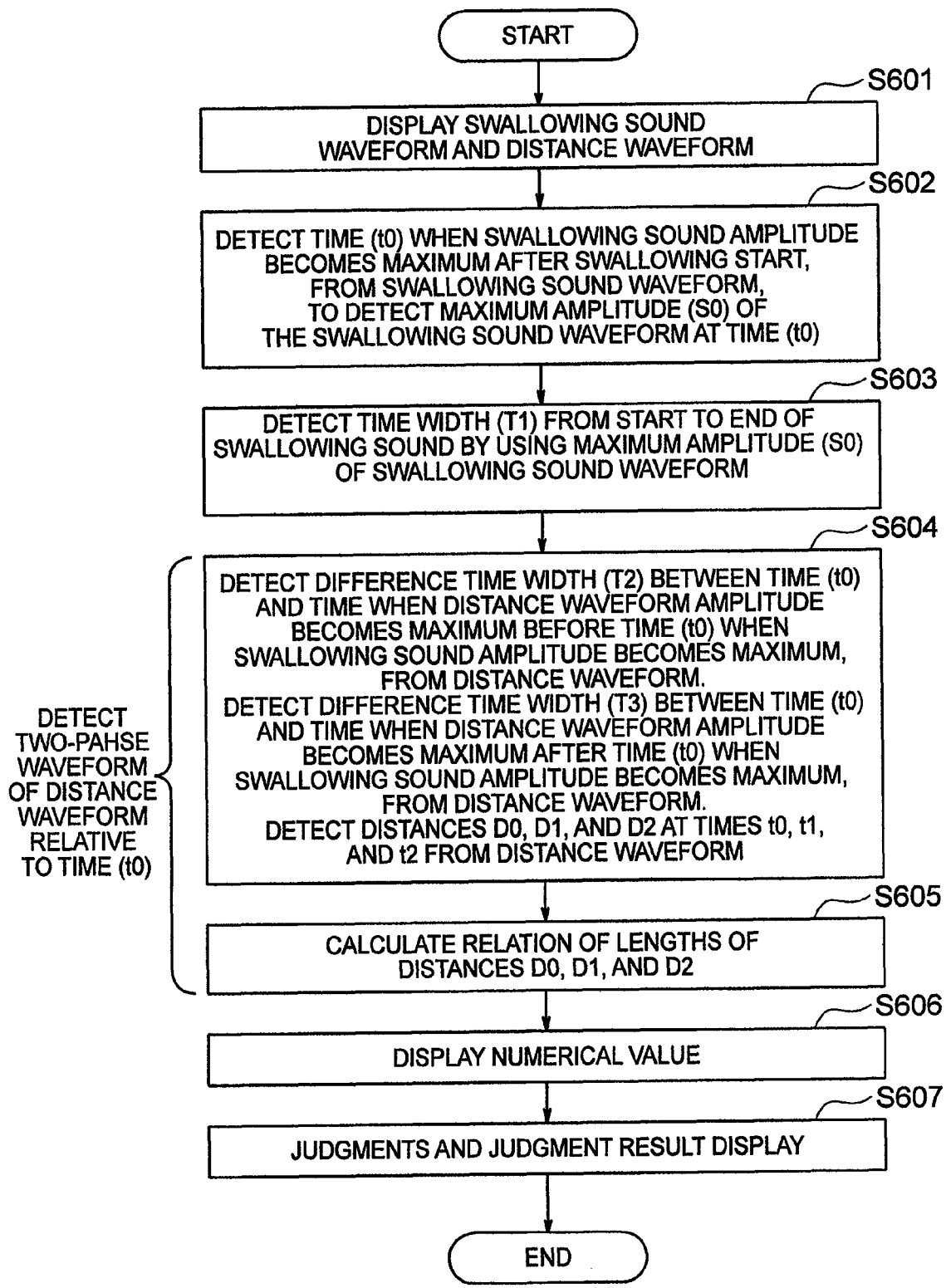
FIG. 6 is a flow chart illustrating a method of detecting a time parameter, a distance voltage and a maximum amplitude of a swallowing voice.
Figure 7:
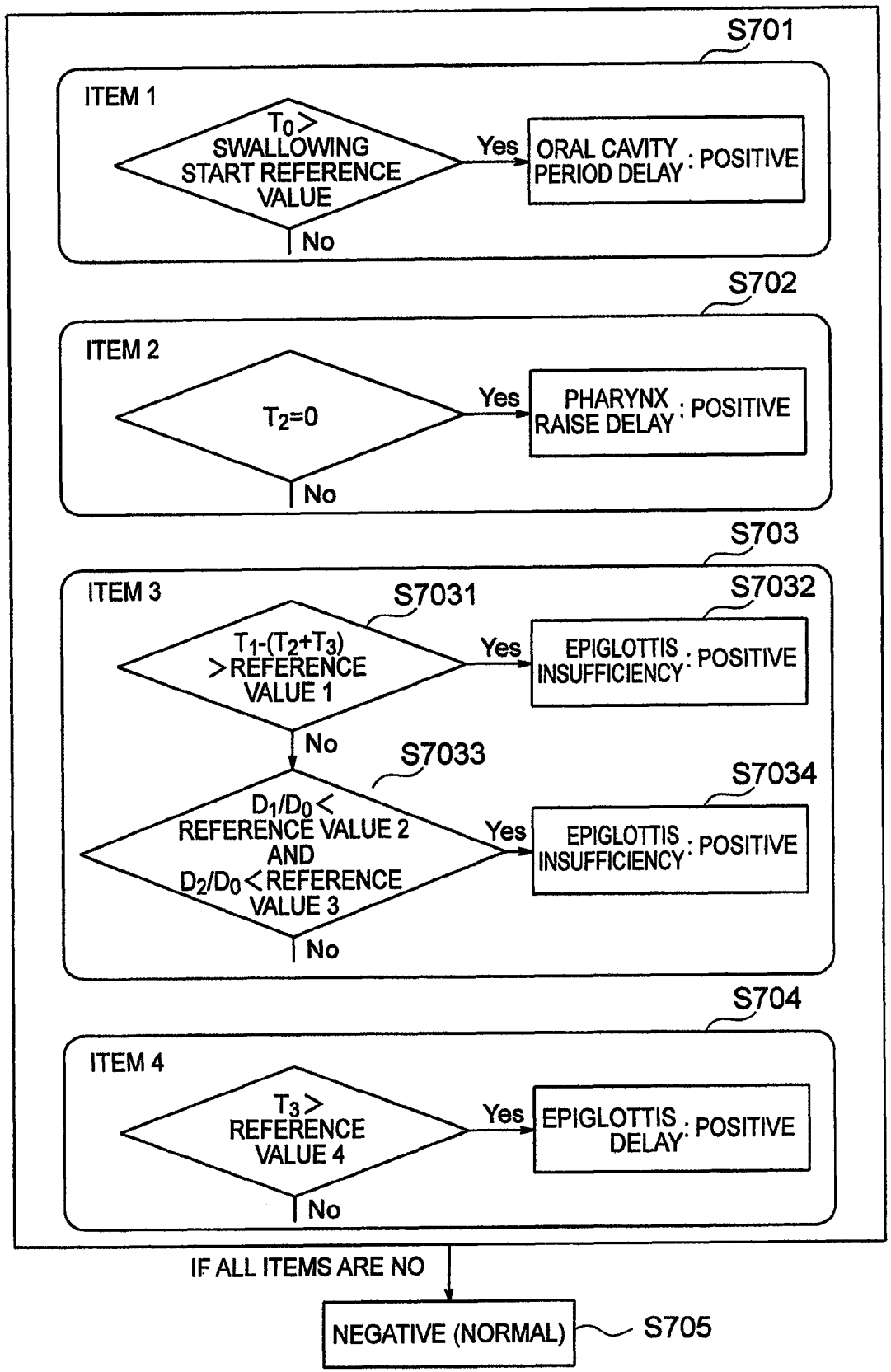
FIG. 7 is a diagram illustrating examples of dysphagia judgment and judgment result display.

FIG. 7 is a diagram illustrating an example of judgments of dysphagia and judgment result display (corresponding to Step S607 illustrated in FIG. 6). Judgments and the like are performed by the processor 1081 of the data processor unit 108. The method of performing judgments and displaying the judgment results is not limited to the method illustrated in FIG. 7, but items necessary for clinical purposes may be added or deleted as desired to obtain an optimum judgment method and display method. As illustrated in FIG. 7 (and FIGS. 5 and 6), all judgments by the judgment method are performed by calculating feature amounts of the distance waveform by using the reference time ($t_0$) extracted from the swallowing sound waveform.

In FIG. 7, four items are judged. At Step S701 for the first item, a swallowing start reference value (e.g., 1 second) is compared with the time width To from the swallowing start time (0) (when the button 106 is operated) to the swallowing sound maximum peak time. If it is judged that $T_0$ is longer than the swallowing start reference value (Yes), it is judged that an oral cavity period (swallowing time) delay is positive, and "oral period delay: positive" is displayed.

At Step S702 for the second item, it is judged whether the difference time width ($T_2$) is 0. That the time width ($T_2$) is zero (Yes) means that the waveform is a single peak waveform and no peak exists before the time ($t_0$). It is therefore judged that a pharynx raise delay is positive, and "pharynx raise delay: positive" is displayed.

At Step S703 for the third item, judgment of larynx insufficiency is performed by two approaches.

With the first approach, at Step S703 for the third item, it is judged whether the value of the time width $T_1$ from the start to end of a swallowing sound subtracted by a addition value of the difference time widths $T_2$ and $T_3$ is longer than a first reference value (e.g., 0.1 sec) (Step S7031). If longer (Yes), it is judged that epiglottis insufficiency is developed terminating a motion of the epiglottis earlier than the alimentary bolus passes through, and "epiglottis insufficiency: positive" is displayed. If shorter than the first reference value (No at Step S7031), as the second approach to checking the two-phase waveform, it is judged whether the ratio $D_1/D_0$ is smaller than a second reference value (e.g., 1.1) and the ratio $D_2/D_0$ is smaller than a third reference value (e.g., 1.2) (Step S7033). If smaller (Yes), it is judged that epiglottis insufficiency is developed not recognizing the two-phase waveform, and "epiglottis insufficiency: positive" is displayed (Step S7034).

For the fourth item, if the difference time width $T_3$ is longer than a fourth reference value (e.g., 0.5 sec) (Yes), it is judged that epiglottis delay is developed, and "epiglottis delay: positive" is displayed (Step S704). If all the first to fourth items are "No", it is judged as negative (normal) and all the items are displayed as negative (Step S705).

Judgments and judgment result display of dysphagia can be performed in the manner described above.

Next, description will be made on a motion of the larynx and pharynx during swallowing with reference to FIG. 8 (refer to other drawings when necessary). Description will be made first on the state in the body of a test subject M during swallowing with reference to FIG. 8 at (a) to (e), and thereafter on the distance between the oscillation coil 101 and detection coil 101 with reference to FIG. 8 at (a1) to (e1) corresponding to FIG. 8 at (a) to (e), respectively. (a) to (e) in FIG. 8 correspond to the times $t_3$, $t_1$, $t_0$, $t_2$ and $t_4$, respectively. The times $t_3$ and $t_4$ correspond to times immediately before and after the distance waveform (refer to FIG. 5) changes. (a1) in FIG. 8 is a schematic diagram drawn by viewing the test subject M at (a) in FIG. 8 along an arrow direction A, and this relation is also applied to (b1) to (e1) in FIG. 8.

As illustrated in (a) of FIG. 8, at the time $t_3$ a nasal cavity 802 expands inside a nose 801 of the test subject M, and teeth 805 and an oral cavity 803 exist inside a mouth 804. An alimentary bolus F is on a tongue 806. A larynx 807 exists in a lower portion of a pharynx 811. An epiglottis 810 of the larynx 807 directs upward. The nasal cavity 802 communicates with an air way 808, and an esophagus is closed. The oscillation coil 101 and detection coil 102 are disposed on both sides of a thyroid cartilage 100, and the microphone 103 is disposed just under the coils.

As shown in (b) of FIG. 8, at the time $t_1$ the alimentary bolus F is transported to the larynx 807, and the thyroid cartilage 100 moves upward, and the epiglottis 810 moves downward in order to block a path from the nasal cavity 802 to the air way 808. If the motion or the like of the tongue is not normal, transport of the alimentary bolus F from the oral cavity 803 to larynx 807 is not performed normally (taking time).

As shown in (c) of FIG. 8, at the time to the epiglottis 810 blocks a path from the nasal cavity 802 to air way 808, and the alimentary bolus F passes sidewise the epiglottis 810. In this case, the thyroid cartilage 100 moves forward (in the direction that the face of the test subject M is directed). If a motion of the epiglottis 810 is not normal, the path from the nasal cavity 802 to air way 808 is not blocked completely, and a portion of the alimentary bolus F enters (is aspirated into) the air way 808.

As shown in (d) of FIG. 8, at the time $t_2$ the alimentary bolus F completely passes sidewise, the epiglottis 810 starts moving upward to recover the initial position, and the thyroid cartilage 100 moves backward to take the same position as that illustrated in FIG. 8(b).

As shown in (e) of FIG. 8, at the time $t_4$ the alimentary bolus F completely passes sidewise the larynx 807, and the epiglottis 810 and thyroid cartilage 100 recover the original positions (same as those illustrated in FIG. 8(a).

During such a swallowing operation, the distance between the oscillation coil 101 and detection coil 102 changes from L1 to L5 as illustrated in (a1) to (e1) of FIG. 8. The reason why the distance L3 illustrated in (c1) of FIG. 8 is longer than L1 may be ascribed to a bump of the larynx caused by a forward motion of the thyroid cartilage 100 due to the block by the epiglottis 810, a motion of an arytenoid cartilage (not shown) inside the thyroid cartilage 100 to a median, an inversion of the epiglottis 810, an inversion of a vocal code (not shown), and the like. Namely, expansion from the distance L2 to L3 corresponds to a normal operation of the epiglottis 810, and if this expansion does not occur, it is considered that insufficiency of the epiglottis 810 is developed.

Tension of the epiglottis 810 is slightly relaxed at the time $t_2$, and the distance L4 recovers approximately the same distance (L2) at the time $t_1$. Since this change occurs, a healthy person has a two-phase waveform. The living body inspection apparatus 1000 of the embodiment can correctly judge dysphagia from how the two-phase waveform is distorted, a time delay, and a deformed shape.

The living body inspection apparatus 1000 of this embodiment can easily inspect dysphagia and display inspection results in the manner described above. Namely, the living body inspection apparatus 1000 can realize a solving method suitable for clinical sites in which a test subject M is inspected easily in accordance with characteristic motions of the test subject M during swallowing.

In the living body inspection apparatus 1000, a swallowing sound is subjected to a full wave rectification process by the full wave rectifier circuit 210 to detect an envelope from the LPF circuit 211 so that features of the swallowing sound can be extracted easily.

Further, by using the button 106, the swallowing state time can be detected easily.

Furthermore, the living body inspection apparatus 1000 displays the distance waveform and swallowing sound waveform at the same time, together with various numerical values calculated by using the swallowing sound peak time as a reference. It is therefore possible to judge visually and quantitatively dysphagia caused by advanced age, brain diseases and the like.

Still further, it is sufficient that a test subject M mounts only the flexible holding members 109 and 110 so that the test subject less feels discomfort and malaise than a conventional method mounting electrodes and the like.

The embodiments have been described above. The invention is not limited to the embodiments.

For example, acceleration sensors may be used instead of the oscillation coil and detection coil to detect a lateral displacement of larynx of a test subject.

The living body inspection apparatus of the present invention may by used for visualizing the effects of rehabilitation for dysphagia.

The flexible holding member for holding the oscillation coil, detection coil or microphone may be equipped with an adjuster for absorbing individual differences of sizes of necks of test subjects.

Each reference value may be preset by medical doctors or the like, or may be an average of data of a plurality of healthy persons obtained through statistics.

Other specific structures of the invention may be modified, as required, without departing from the spirit of the present invention and the scope of the appended claims.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A living body inspection apparatus comprising:
a larynx displacement detector including a pair of sensor parts which are separately held on the surface of a subject at lateral positions of a larynx of the subject for detecting a distance along a lateral direction between the lateral positions of the larynx;
a swallowing sound detector for detecting a swallowing sound generated when said subject swallows;
displaying means for displaying a waveform regarding a displacement of said larynx and formed in accordance with information of the distance between the lateral positions obtained from said larynx displacement detector, and a waveform regarding said swallowing sound and formed in accordance with information obtained from said swallowing sound detector;
processing means for instructing said displaying means; and
a flexible holding member,
wherein said flexible holding member includes a pair of flexible sensor holding members and a mounting member,
said pair of sensor holding members are at respective ends thereof, and are each provided with a respective one of said sensor parts of said larynx displacement detector,
one of said sensor holding members is further provided with said swallowing sound detector, and
said mounting member has a pair of arms which are respectively formed integrally with said pair of sensor holding members at other ends thereof to hold said pair of sensor holding members, and said arms are configured so that said arms can be opened and hold the neck of the subject and so that said pair of sensor parts are respectively held at the lateral positions of said larynx of said subject.

2. A living body inspection apparatus comprising:
larynx displacement detecting means for detecting a displacement of two positions in a lateral direction of a larynx of a subject;
swallowing sound detecting means for detecting a swallowing sound generated when said subject swallows;
displaying means for displaying a waveform regarding the displacement of two positions of said larynx and formed in accordance with information obtained from said larynx displacement detecting means and a waveform regarding said swallowing sound and formed in accordance with information obtained from said swallowing sound detecting means;
processing means for instructing said displaying means; and
a flexible holding member,
wherein said flexible holding member includes a pair of sensor holding members having flexibility and a mounting member,
said pair of sensor holding members are at one ends thereof, provided with said larynx displacement detecting means and said swallowing sound detecting means, and
said mounting member is integrally formed with said pair of sensor holding members at other ends thereof to hold said pair of sensor holding members and said other ends are made open so that said mounting member is mounted on and held by said larynx of said subject;
wherein said pair of sensor holding members and said mounting member are made of different members and have a connection structural body integrally coupling said mounting member to said sensor holding members at the other ends, and said flexible holding member is mounted on and held by said larynx of said subject.

3. The living body inspection apparatus according to claim 1, wherein said pair of sensor holding members are disposed inwardly with respect to said mounting member.

4. The living body inspection apparatus according to claim 3, further comprising an abutting member disposed at ends of said mounting member to be abutted upon said larynx of said subject.

5. The living body inspection apparatus according to claim 1, wherein:
said swallowing sound detector includes a microphone to be disposed on said larynx of said subject during inspection;
said pair of sensor parts are an oscillation coil and a detection coil; and
said processing means identifies a peak time of said swallowing sound in accordance with an envelope line of a signal supplied from said microphone, and calculates either a time when a minimum value of a distance between the lateral positions of said larynx is obtained before said identified peak time or a time when a minimum value of a distance between the lateral positions of said larynx is obtained after said identified peak time, in accordance with an envelope line of an output signal from an amplifier circuit for amplifying a voltage induced in said detection coil by said oscillation coil.

6. The living body inspection apparatus according to claim 5, further comprising a full wave rectifying means connected to said microphone and a low-pass filter, wherein said processing means detects the swallowing sound in accordance with a signal from said microphone full-wave rectified by said full wave rectifying means and low frequency components thereof being passed through said low-pass filter.

7. The living body inspection apparatus according to claim 5, wherein said oscillation coil and said detection coil are disposed on respective sides of a thyroid cartilage of said larynx of said subject.

8. The living body inspection apparatus according to claim 1, wherein said processing means judges from the waveform regarding the displacement of said larynx whether the distance between the lateral positions has two peaks.

9. The living body inspection apparatus according to claim 5, wherein by using the peak time of said swallowing sound as a reference, said processing means judges whether each of a time difference from a time when an operating member is operated, a time difference from a time when a minimum value of a distance between the lateral positions of said larynx is obtained before the peak time of said swallowing sound, and a time when a minimum value of a distance between the lateral positions of said larynx is obtained after the peak time of said swallowing sound is in each of corresponding reference ranges, and instructs said displaying means to display judgment results.

10. The living body inspection apparatus according to claim 5, wherein said oscillation coil and said detection coil are held at approximately facing or parallel positions, and said oscillation coil and said detection coil are disposed in a perpendicular relation relative to said microphone.

11. A living body inspection apparatus comprising:
larynx displacement detecting means for detecting a displacement of two positions in a lateral direction of a larynx of a subject;
swallowing sound detecting means for detecting a swallowing sound generated when said subject swallows;
displaying means for displaying a waveform regarding the displacement of two positions of said larynx and formed in accordance with information obtained from said larynx displacement detecting means and a waveform regarding said swallowing sound and formed in accordance with information obtained from said swallowing sound detecting means;
processing means for instructing said displaying means; and
a flexible holding member,
wherein said flexible holding member includes a pair of sensor holding members having flexibility and a mounting member,
said pair of sensor holding members are, at one ends thereof, provided with said larynx displacement detecting means and said swallowing sound detecting means,
said mounting member is integrally formed with said pair of sensor holding members at other ends thereof to hold said pair of sensor holding members and said other ends are made open so that said mounting member is mounted on and held by said larynx of said subject,
said swallowing sound detecting means includes a microphone to be disposed on said larynx of said subject during inspection,
said larynx displacement detecting means includes an oscillation coil and a detection coil, and
said processing means identifies a peak time of said swallowing sound in accordance with an envelope line of a signal supplied from said microphone, and calculates either a time when a minimum value of a distance between two positions of said larynx is obtained before said identified peak time or a time when a minimum value of a distance between two positions of said larynx is obtained after said identified peak time, in accordance with an envelope line of an output signal from an amplifier circuit for amplifying a voltage induced in said detection coil by said oscillation coil.

12. The living body inspection apparatus according to claim 11, further comprising a full wave rectifying means connected to said microphone and a low-pass filter, wherein said processing means detects the swallowing sound in accordance with a signal from said microphone full-wave rectified by said full wave rectifying means and low frequency components thereof being passed through said low-pass filter.

13. The living body inspection apparatus according to claim 11, wherein said oscillation coil and said detection coil are disposed on both sides of a thyroid cartilage of said larynx of said subject.

14. The living body inspection apparatus according to claim 11, wherein said processing means judges from the waveform regarding a displacement of the two positions of said larynx whether the two positions have two peaks.

15. The living body inspection apparatus according to claim 11, wherein by using the peak time of said swallowing sound as a reference, said processing means judges whether each of a time difference from a time when an operating member is operated, a time difference from a time when a minimum value of a distance between two positions of said larynx is obtained before the peak time of said swallowing sound, and a time when a minimum value of a distance between two positions of said larynx is obtained after the peak time of said swallowing sound is in each of corresponding reference ranges, and instructs said displaying means to display judgment results.

16. The living body inspection apparatus according to claim 11, wherein said oscillation coil and said detection coil are held at approximately facing or parallel positions, and said oscillation coil and said detection coil are disposed in a perpendicular relation relative to said microphone.

* * * * *